United States Patent
Cantwell

[11] Patent Number: 6,000,403
[45] Date of Patent: Dec. 14, 1999

[54] OXYGEN BANDAGE

[76] Inventor: Evelyna Dyson Cantwell, 101 Hickory Hill Rd, Chadds Ford, Pa. 19317

[21] Appl. No.: 09/000,318
[22] PCT Filed: Jul. 30, 1996
[86] PCT No.: PCT/GB96/01856
§ 371 Date: May 6, 1998
§ 102(e) Date: May 6, 1998
[87] PCT Pub. No.: WO97/04831
PCT Pub. Date: Feb. 13, 1997

[30] Foreign Application Priority Data
Aug. 2, 1995 [GB] United Kingdom ............ 9515807

[51] Int. Cl.$^6$ ............................................. A61R 13/00
[52] U.S. Cl. ................................. 128/888; 602/41
[58] Field of Search ........................... 128/846, 888, 128/889; 602/41–59

[56] References Cited

U.S. PATENT DOCUMENTS

| 4,699,146 | 10/1987 | Sieverding | 602/52 |
| 4,909,244 | 3/1990 | Quarfoot | 602/48 |
| 5,106,629 | 4/1992 | Cartmell | 602/48 |
| 5,322,695 | 6/1994 | Shah | 602/54 |

Primary Examiner—Michael A. Brown
Attorney, Agent, or Firm—Norman E. Lehrer

[57] ABSTRACT

A topical hyperbaric bandage having a gas diffusion resistant flexible and/or resilient sheet material and including an adhesive layer adapted to be affixed to the skin. The adhesive layer is adapted to surround a treatment area, at least one release layer disposed over the adhesive layer and a device that supplies a therapeutic gas to the treatment area. The bandage is adapted to retain a single charge of therapeutic gas over a treatment period. The bandage includes a reservoir and a device for opening the reservoir.

11 Claims, 1 Drawing Sheet

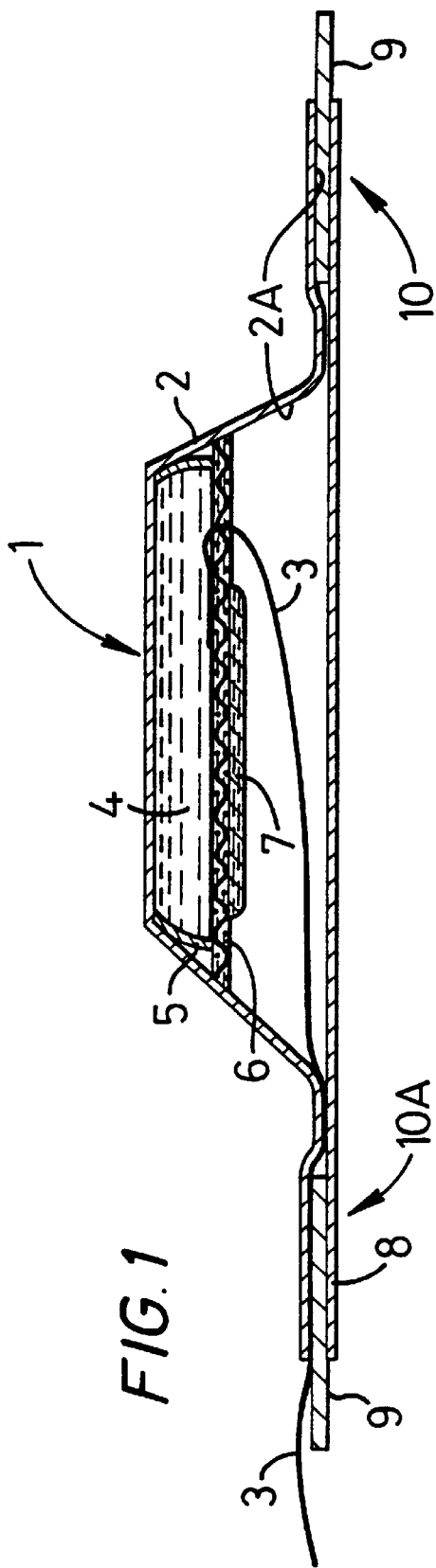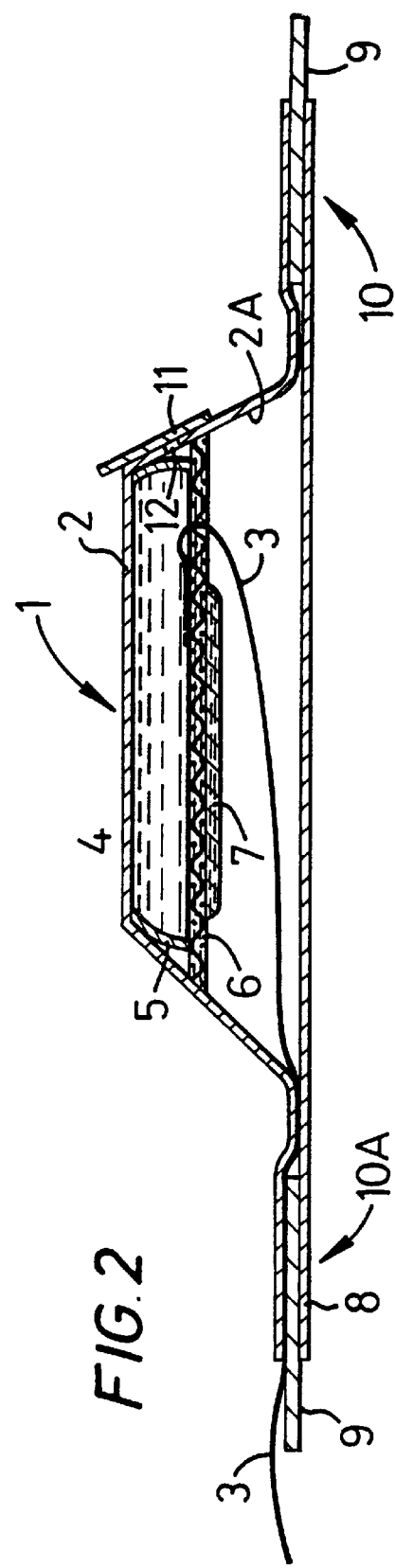

OXYGEN BANDAGE

The present invention relates to a topical hyperbaric bandage and to a method of wound healing utilising the same.

Hyperbaric apparatus for the treatment of open wounds and lesions by application thereto for therapeutic gas such as oxygen with or without a pharmacologically acceptable additive is generally known. For example in U.S. Pat. No. 5,154,697 and U.S. Pat. No. 4,801,291 there are described various arrangements for the treatment of open lesions in wounds in a hyperbaric chamber with oxygen which promotes granulation, raises capillary blood oxygen levels and elevates redox potential thereby suppressing bacterial growth and encouraging revascularisation.

In my earlier patent Application, WO94/21323 I have described a topical hyperbaric bandage comprising a gas diffusion resistant flexible and/or resilient sheet material including an adhesive layer to be fixed to the skin, said adhesive layer surrounding the treatment area, at least one release layer disposed over the adhesive layer and means for supplying a therapeutic gas to the treatment area, the device being adapted to retain a single charge of a therapeutic gas over a treatment period. The device may be further adapted such that it is rechargeable at least once with therapeutic gas for a repeat treatment whilst the device is in situ.

The advantage of arrangements of this type is that since previously hyperbaric treatment was only available in suitably equipped hospitals, the arrangement according to my earlier application allowed the translation of hyperbaric treatment to the domestic sphere. This is because not only were the hyperbaric devices small, but also the oxygen supply required was much smaller than had hitherto been the case.

Hyperbaric oxygen treatment has been somewhat controversial in the past because of the problems with oxygen toxaemia. We have found that relatively small super-atmospheric pressures of for example 1.03 to 1.04 atmospheres are effective to assist in revascularisation as long as the treatment does not go on too long. For example, treatments of many conditions, e.g. bedsores, for much longer than four hours at one time may well induce oxygen toxaemia and hence be counterproductive. Our previous invention was based on the proposition that only a single charge of oxygen was not only necessary but highly desirable. Although, the single charge may be repeated after a few days or even after a few hours if required. The previous practice of flowing oxygen over a lesion for an indeterminate period was not only unnecessary, but clinically counterproductive.

One attempt at producing such a bandage is to be found in GB-A-2024012. This reveals a two-part storable topical hyperbaric wound dressing which comprises a peroxy compound such as hydrogen peroxide and an agent for activating the same to produce oxygen. Both components are absorbed or disposed on juxtaposed sheets and rely on either moisture from the wound to achieve activation or from the crushing of microspheres of the initiator prior to assembly about the wound.

This arrangement is not satisfactory in part because the peroxy compounds are so labile when not liquid. Although they may be absorbed on a particular material experimentally, storage in commercial conditions results in the peroxy compound deteriorating rapidly. This is particularly so a higher temperatures.

What is required therefore is a hyperbaric bandage which is ready to use, easy to store and reliable. This is achieved in part by providing a liquid reservoir of the peroxy compound. A catalyst may not be required as such because haemoglobin from the wound may act as the necessary catalyst in some circumstances.

The present invention is characterised in that the topical hyperbaric bandage comprises a reservoir for a source of therapeutic gas in liquid form and in that gas release from the reservoir is initiable after the bandage has been secured to the skin. It will be appreciated that the therapeutic gas in non-gaseous form is most usually stored in chemical form and is released by a biologically acceptable reaction which occurs within the device on actuation.

Thus the hyperbaric bandage may comprise a biologically acceptable means for a support of a reducing metal or other catalyst or other reactive material, physically separated from the store but juxtaposed thereto. The therapeutic gas is usually mainly oxygen, the biologically acceptable support is most preferably an antiseptic pad secured or free within the bandage adjacent the proposed treatment area. The catalyst may include compounds containing transition metals.

The source of therapeutic gas is preferably antiseptic itself in its stored form and is hyperbaric on release to the treatment area. One example of a therapeutic gas of this type is oxygen emanating from the reaction of hydrogen peroxide, catalysed by a reducing metal catalyst such as zinc or copper or indeed, any other biologically acceptable reducing metal catalyst. Alternatively, the catalyst may be haemoglobin itself which it is to be found in fresh wounds. In which case, either no separate catalyst is required, or such catalyst that is required is for secondary or back-un use.

The reservoir may comprise release means operable after the bandage is secured to the skin to provide communication between the reservoir and the treatment area enclosed by the secured bandage; the establishment of communication serving to initiate the release of hyperbaric gas. One such means is a drawstring moulded integrally with a store or reservoir such that it will open the reservoir to release a fluid into the treatment area to initiate gas generation. Alternatively, an adhesively attached aluminium foil can be employed. It will be appreciated that the remote end of the drawstring or foil may be secured between the release layer and the adhesive layer prior to the securing of the bandage to the skin, and that a firm pull on the remote end of the drawstring will have the effect of ripping open or otherwise puncturing the reservoir to release a liquid peroxy compound such as hydrogen-peroxide or percarbonate, stabilized if necessary, so that the liquid flows into contact with a zinc or copper catalyst deposited on a gauze to produce both free oxygen and water.

In a particularly preferred form of the invention the dressing or gauze may comprise a pharmaceutically acceptable humectant, for example TPH hydrophilic polymer (trade name), to bind water molecules on generation. The TPH hydrophilic polymer belongs to a family of hydrophilic polyether polyurethanes and is particularly suited to this application because of its hydrophilic and gas permeable properties. The TPH hydrophilic polymer can be further used for a two part bandage whereby the TPH polymer dressing is adapted to remain in situ when the rest of the bandage is removed. When a repeat hyperbaric treatment is required, a new hyperbaric bandage, but without a dressing, can be placed directly on top of the TPH polymer dressing without disturbing the wound.

Also, the TPH polymer may be impregnated with an appropriate anti-bacterial such that it can act as a bandage in-itself once it is separated from the hyperbaric device, and a normal surgical dressing is no longer required. Other matrices with the properties of gas permeability and/or hydrophilicity may also be used in a similar fashion.

The hyperbaric bandage may be adapted to be rechargeable with a source of therapeutic gas on at least one occasion. In a preferred embodiment, there is provided an air-tight resealable vent on the upper surface of the bandage. A fresh supply of for example hydrogen peroxide can be injected through the vent directly onto the dressing comprising the catalyst. Upon contact with the catalyst the therapeutic oxygen is released into the wound.

The therapeutic gas such as oxygen supplied to the treatment area may be heated to a temperature between 20° C. and 44° C., preferably between 32° C. and 39° C. and more preferably about 37° C. This heating may be conveniently achieved by arranging that the peroxy-compound catalysis is exothermic. In such an arrangement, the gas diffusion resistant material may be double walled, as in bubble film, to retain heat as far as possible.

The present invention will now be described by way of illustration only with reference to the accompanying drawings wherein:

FIG. 1 shows a vertical cross-section through a device of the invention.

FIG. 2 shows a vertical cross-section through a device of the invention comprising a resealable vent.

With reference to FIG. 1 a topical hyperbaric bandage (1) is provided with a gas-impermeable flexible and/or resilient material (2) which is preferably a transparent plastics material such as a polyalkylene, polythene or PVC sheet in the general form of a rectangle or square having a dimension of for example 100 mm by 120 mm. The sheet material may be formed by non-elastic stretching or thermo-forming with a pocket over the treatment area to retain a dressing therein, or merely to provide a greater area of containment of therapeutic gas.

The sheet material (2) is formed over the entirety of its lower surface with a first adhesive layer (2A) whereas the upper layer is essentially non-adhesive. The first adhesive layer (2A) is a thin hydrocolloid adhesive having a thickness preferable of 0.45 mm. Other suitable materials for adhering bandages for wound dressings etc. may be used with a thickness ranging between 0.20–0.60 mm.

Centrally disposed on the underside of the sheet material (2) is a gas/liquid-impermeable reservoir material (5) containing a liquid chemical reservoir of releasable therapeutic oxygen such as hydrogen peroxide (4). Other chemically stored forms of releasable therapeutic oxygen may also be used. The reservoir (5) is made of resilient and/or flexible plastics material and is adhered to the underside of the sheet material (2) with the adhesive layer (2A).

Juxtaposed below the reservoir (5), and preferably extending over the operative area is a gauze or dressing (6) of a pharmacologically acceptable foamed material impregnated with a catalyst or reaction activator such as a transition metal compound. The dressing (6) may alternatively be a traditional multi-layer woven material. The dressing (6) extends beyond the periphery of the reservoir (5) such that its exposed upper surface is fixedly adhered to the underside of the sheet material (2) with the adhesive layer (2A). Alternatively the dressing may be omitted along with the catalyst or reaction activator since haemoglobin from the wound will act as a catalyst for the peroxy compounds.

Integral with the reservoir material (5) there is a release means (3), preferably a strong string, the first end of said string or foil (3) being detachably attached to the reservoir material (5) along a line of weakness such that when the string (3) is pulled, the reservoir material (5) tears to release the hydrogen peroxide (4) onto the dressing (6). The string (3) is threaded through or over the dressing (6) and then between the adhesive layer (2A) of the sheet material (2) and a secondary release layer (9) (described below) such that an adequate portion of the string (3) extends beyond the secondary release layer (9) to leave the second end of the string (3) a free end. Alternative release means may also be used such that the air-tight seal over the operative area is not compromised such as aluminium foil disposed over a preformed aperture.

To the underside of the edges of the sheet material (2) is applied a primary release layer (8) which is secured to the adhesive layer (2A) on the underside of the sheet material (2), and generally conforms to the exterior periphery thereof. The release layer is an essentially non-adhesive layer which forms a weak bond with the adhesive layer (2A) disposed on the underside of the sheet material (2). In the arrangement shown in FIG. 1 the release layer is formed in a two layer partially overlapped configuration, whereby the removal of the primary release layer (8) allows a portion of the adhesive face to be exposed for contact with the skin about the wound. A secondary release layer (9) is secured to each parallel side of the sheet material (2). This arrangement allows the device to be correctly orientated relative to the wound and secured in this orientation while the second release layer (9) or layers are removed so that the device is correctly orientated on the skin without folds or rucks. In the arrangement as shown in FIG. 1 the edge portions of the primary release layer (8) do not adhere to the underside of the sheet material (2) but are left free. The secondary release layer (9), however, is adhered to the remaining underside on each parallel side of the sheet material (2) in between the primary release layer (8) and the sheet material (2).

Optionally, the dressing (6) may further comprise a layer of humectant or inert hygroscopic material (7) on the side not in contact with the reservoir (5). This enables any residual water resulting from a chemical reaction to be absorbed and allows the wound area to remain dry. Whether the addition of the hygroscopic material (7) is required will be determined by the type of reaction used to release the therapeutic gas from a stored form.

In an alternative arrangement the topical hyperbaric bandage (1) may be in two parts such that the sheet material (2) can be removed after hyperbaric treatment of the wound area whilst the dressing (6) is left in situ. Thus the lesion is not disturbed during repeated treatments. The dressing may be impregnated with an appropriate anti-bacterial composition to prevent the lesion from becoming infected or septic. When the next hyperbaric treatment is required, a new bandage (1) but without the dressing (6) can be applied directly on to the dressing (6) from the previous treatment. The dressing (6) for use in this manner is suitable for several repeat treatments. Specifically, the dressing in this embodiment is a hydrophilic polymer which belongs to a family of hydrophilic polyether polyurethanes and is currently marketed under the trade name TPH hydrophilic polymer. The TPH polymer is a gas permeable matrix and is also hydrophilic. These properties are particularly suited for this invention, since the TPH polymer can absorb the water released from the hydrogen peroxide reaction and since the polymer is gas permeable, the hyperbaric treatment is unhindered.

With reference to FIG. 2, in an alternative arrangement of a hyperbaric bandage there may be a resealable vent (12) on the upper surface of the sheet material (2). The air-tight seal is achieved with for example a second layer of adhesive sheet material (11). The vent allows access to the dressing (6) and the space therebelow only. Thus, when a repeat hyperbaric treatment is required, the second layer of sheet material (11) is removed and a given quantity of hydrogen peroxide injected onto the dressing. The second layer of sheet material (11) is replaced immediately to reseal the vent (12) and prevent escape of evolved oxygen. The fresh hydrogen peroxide reacts with the catalyst in the dressing (6) to evolve the therapeutic oxygen.

Further, during application of the bandage to the skin, the vent (12) may be opened and the raised portion of the bandage compressed against the skin to expel as much air as possible, prior to the release of the hydrogen peroxide, thereby to allow the space between the dressing (6) and the lesion to fill with a greater proportion of released oxygen.

The hyperbaric device (1) is applied to a preferably dirt and grim free, smoothed or pre-shaven skin. The first underside (10) of the hyperbaric device (1) is the side not comprising the free end of the string (3) whereas the second underside (10A) of the hyperbaric device (1) comprises the free end of the string (3). The said first underside (10) is fixed onto the pre-treated skin first by peeling off both the first release layer (8) and the second release layer (9). Then whilst firmly pressing the sheet material (2) on the second underside (10A) onto the skin, the remaining secondary release layer (9) is peeled off. Once the hyperbaric device (1) is thus securely in position the free end of the string (3) can be pulled out firmly from the second underside (10A) which forms an air-tight seal between the sheet material (2) and the skin.

Upon thus pulling the string (3) the reservoir (5) tears to release the hydrogen peroxide (4) onto the catalyst impregnated in the dressing (6). The ensuing chemical reaction between the hydrogen peroxide and the reducing metal catalyst, releases a charge of oxygen over a period of about 5 to 20 minutes. The released oxygen is trapped within the gas-impermeable sheet material (2) and thereby creates a small super-atmospheric pressure of around 1.03 to 1.04 atmospheres thereby being bought into contact with the wound. The water resulting from such a chemical reaction may be absorbed into the inert hygroscopic material (7).

The quantity of hydrogen peroxide in the reservoir is determined by the amount of oxygen required to effectively treat a given lesion. For example 1 ml of 2M $H_2O_2$ will release sufficient oxygen to create a pressure of around 2.20 atmospheres within the enclosed device where the dimensions of the enclosed volume are 5 cm by 2 cm by 1 cm deep. However, it is estimated that since at least 40% to 60% of the released oxygen will be lost through seepage, absorption into surrounding materials, incomplete reaction and natural diffusion, there will be a working pressure of at least 1.03 atmospheres which is more than sufficient to allow a charge of oxygen to enter the wound.

By suitable adjustment of the quantities of hydrogen peroxide in relation to the volume of enclosed area between the wound and the device (1) when fixed in position, the problem of hypoxia and over inflation of the hyperbaric device (1) is avoided.

Devices in accordance with the present invention may thus be applied such as to reduce hypoxia but avoid oxygen toxaemia. Typical regimes such as one treatment of 20 minutes to 2 hours duration twice a day to repeated treatments over several days allow wounds and lesions to cure quickly.

Each device is for a single use and is disposable after one use. Optionally, in a second embodiment, there may be a facility for injecting a given quantity of fresh hydrogen peroxide into the device, to recommence the reaction.

It will be appreciated that because of the portable nature of the device and the ease of use, patients with lesions can apply the device to the wound themselves without the need for professional medical intervention. Accordingly, the arrangement of the present invention is cheap and easy enough to use to bring hyperbaric treatment more widely into use.

The invention provides, therefore a topical hyperbaric device for a single application; a disposable device comprising a self-contained liquid store of therapeutic gas such as oxygen, said gas being released into the wound upon chemical activation by a catalyst or by the catalytic action of haemoglobin.

I claim:

1. A topical hyperbaric bandage (1) comprising a gas diffusion resistant flexible and/or resilient sheet material (2) including an adhesive layer (2A) adapted to be affixed to the skin, said adhesive layer adapted to surround a treatment area, at least one release layer (8,9) disposed over said adhesive layer, and means (5,6,3) for the supply of therapeutic gas to the treatment area, said bandage being adapted to retain a single charge of therapeutic gas over a treatment period;

characterised in that said bandage comprises a reservoir (5) for a source (4) of therapeutic gas in liquid form, and means (3) for opening the reservoir (5) after the bandage has been affixed to the skin to initiate the supply of said therapeutic gas to the treatment area.

2. A bandage according to claim 1 wherein the bandage comprises a biologically acceptable means (6) for the support of a compatible reducing metal catalyst, physically separated from the contents of the reservoir (5) but disposed so as to communicate with the source (4) once the reservoir (5) has been opened.

3. A bandage according to claim 2 wherein the therapeutic gas is mainly oxygen and wherein the biologically acceptable support is an antiseptic gauze or pad (6) within the bandage.

4. A bandage according to claim 3 wherein the source (4) of therapeutic gas is antiseptic in its stored form and hyperbaric on its release effected by the opening of the reservoir (5).

5. A bandage according to claim 4 wherein the source (4) of therapeutic gas is peroxy compound and the catalyst is a biologically acceptable reducing metal.

6. A bandage according to any of claims 2 to 5 wherein the biologically acceptable support (6) comprises a pharmacologically acceptable humectant (7) to bind water molecules.

7. A bandage according to claims 1–5 wherein the means for opening the reservoir (5) is a drawstring (3).

8. A bandage according to claims 1–5 wherein the resevoir (5) can be replaced without the removal of the entire bandage from the skin.

9. A bandage according to claims 2–5, wherein the biologically acceptable support (6) is a hydrophilic polyether polyurethane.

10. A bandage according to claim 1 wherein the reservoir (5) is adapted to be rechargeable with the source (4) of the therapeutic gas for repeat treatments.

11. A bandage according to claim 10 comprising a resealable vent (12).

* * * * *